United States Patent
Hannich et al.

(10) Patent No.: US 7,335,372 B2
(45) Date of Patent: *Feb. 26, 2008

(54) HAIR WAX PRODUCTS CONTAINING POLYETHYLENE GLYCOL WAXES AND HYDROPHOBIC MATERIALS

(75) Inventors: Manuela Hannich, Egelsbach (DE); Michael Franzke, Rossdorf (DE)

(73) Assignee: Wella AG, Darmstadt (DE)

( * ) Notice: Subject to any disclaimer, the term of this patent is extended or adjusted under 35 U.S.C. 154(b) by 372 days.

This patent is subject to a terminal disclaimer.

(21) Appl. No.: 10/704,266

(22) Filed: Nov. 7, 2003

(65) Prior Publication Data

US 2004/0115152 A1   Jun. 17, 2004

(30) Foreign Application Priority Data

Nov. 9, 2002  (DE) .............................. 102 52 167
Jan. 18, 2003 (EP) ................................. 03001081

(51) Int. Cl.
*A61K 8/02*   (2006.01)
*A61K 8/72*   (2006.01)
*A61K 31/74*  (2006.01)

(52) U.S. Cl. .................. 424/401; 424/70.11; 424/78.31
(58) Field of Classification Search ............... 424/401, 424/70.1, 70.11, 70.31
See application file for complete search history.

(56) References Cited

U.S. PATENT DOCUMENTS 3,341,410 A    9/1967   Ochs et al.
4,036,951 A *  7/1977   Halpern et al. ............... 424/60
4,296,763 A   10/1981   Priest et al.
4,938,954 A *  7/1990   Gross et al. ................ 424/70.1
5,194,260 A *  3/1993   Grollier et al. ............. 424/401
5,690,924 A   11/1997   Keil et al.
5,960,924 A * 10/1999   Snyder ...................... 192/85 A
6,475,475 B2* 11/2002   Birkel et al. ............. 424/70.15
2002/0076424 A1* 6/2002  Birkel et al. ................ 424/401
2002/0122811 A1  9/2002  Stein et al.
2002/0164298 A1 11/2002  Birkel et al.

FOREIGN PATENT DOCUMENTS

EP    0 301 197        2/1989
GB    1 563 824        4/1980
GB    1563824       *  4/1980
JP    2002-154937   *  5/2002

OTHER PUBLICATIONS

Answer.com (definition of cream, ointment, and hair wax).*
JP2002-154937 (computer translation).*
D.F. Williams et al: "Chemistry and Technology of Cosmetics and . . . " 2nd Ed, 1996, XP002237428, p. 83.

* cited by examiner

*Primary Examiner*—Sharmila G. Landau
(74) *Attorney, Agent, or Firm*—Michael J. Striker

(57) ABSTRACT

The hair wax product for treating or setting up a human hairstyle has a composition containing more than 20% by weight of one or more waxy polyethylene glycol, which is solid at at 25° C., and at least one additive substance that prevents crystallization of the waxy solid polyethylene glycol. This additive substance preferably is a hydrophobic wax, a hydrophobic soft waxy material or hydrophobic oil and is contained in the product in an amount of more than 5% by weight. Preferred embodiments of the waxy product can contain an emulsifier and/or an additional polyethylene glycol, which is liquid at 25° C.

4 Claims, No Drawings

HAIR WAX PRODUCTS CONTAINING POLYETHYLENE GLYCOL WAXES AND HYDROPHOBIC MATERIALS

BACKGROUND OF THE INVENTION

The subject matter of the present invention is a wax product for treatment of or setting up a human hairstyle. The wax product of the present invention contains a composition comprising a hydrophobic, waxy polyethylene glycol and a hydrophobic substance.

Styling wax compositions are known products for hair treatment. They particularly find application in putting short to medium length hair in a fashionable hairstyle and impart luster, hold as well as stabilize and fix the hair. The hairstyle is also provided with texture and shape with the hair wax. Conventional hair waxes are usually provided in cups or other vessels and their action is based on the following principle: Product is removed with the fingers. The wax is distributed on the surface of the hand and then melted or at least considerably softened by the heat of the hand. It is possible to work the otherwise too hard wax into the hair because of this softening or melting. The wax is worked into the hair in a softened or more or less liquid state. Then it cools and again reaches its original consistency. It hardens and the hairdo obtained has stability and hold and frequently a slightly wet look. Conventional hair wax products, as they are currently offered, are usually formulated on the basis of hydrophobic waxes, fats and oils. They contain a large portion of hydrophobic materials, such as vegetable or animal waxes, fatty acid esters, fatty alcohols, etc. The main components and principal active ingredients are hydrophobic waxes, such as ozocerite, candelilla wax, beeswax, caranauba wax, etc. These types of products have the disadvantage that they are difficult to wash from the hair and comparatively highly load the hair. For that reason hair waxes based on mixture of polyethylene glycol waxes (PEG's) were developed, which are characterized by good water solubility and good washability. For good product performance mixtures of PEG's of different molecular weight must be used. A hair wax is disclosed in EP 0 301 197 A1, which contains a combination of high molecular weight PEG (MW=3000 to 5000), ethoxylated and hydrogenated castor oil and low molecular weight PEG (MW=100 to 300). The disadvantage of this hair wax product is that a crystallization or partial crystallization of the high molecular weight PEG's can occur, which imparts an inhomogeneous grainy appearance to the product. Since the product mass usually fills its container in the heated flowing state, inhomogeneities can occur on cooling, which leads to the wax mass being noticeably softer in the interior of the container than in the outer regions of it.

SUMMARY OF THE INVENTION

It is an object of the present invention to provide a hair wax product, which is characterized by both a good washability and also is less inclined to partial crystallization, which appears uniform over a longer time period and does not appear as grainy as prior art hair wax products.

It is a further object of the present invention to provide a hair wax product which is easily removed from its container, is sufficiently workable, and has good application properties, especially good workability, good distributability and good hairstyle definition.

It is an additional object of the present invention to provide a hair wax product, which imparts luster, hold, fixing and stability to the hair.

It has now been found that these requirements are fulfilled by a hair wax product for treating or setting up a human hairstyle, which contains a hydrophobic substance, which prevents crystallization of polyethylene glycol wax, besides hydrophilic polyethylene glycol wax itself.

The subject matter of the invention is thus a hair wax product with a waxy consistency for treating or setting up a human hairstyle containing (A) more than 20% by weight of at least one waxy solid polyethylene glycol at room temperature; and (B) at least one additive substance that prevents crystallization of the polyethylene glycol (A).

The additive substance (B) preventing crystallization preferably is present in an amount of more than 5% by weight and is preferably selected from the group consisting of hydrophobic waxes, hydrophobic soft waxy materials and hydrophobic oils. The products are preferably water-free, but can also contain small amounts of water, up to a maximum of 15% by weight, preferably a maximum of 10% by weight.

The washability of the product is good in spite of the hydrophobic nature of the additive substance. The usual application properties are not disadvantageously influenced. Unwanted crystallization of the waxy polyethylene glycol in the produce mass is reduced and the consistency is characterized by a better uniformity or greater homogeneity.

The waxy consistency is preferably characterized by a needle penetration number (measurement unit, 0.1 mm; test weight, 100 g; test duration, 5 s; test temperature, 25° C.; according to DIN 51 579) greater than or equal to 10, especially greater than or equal to 20. The solidification point of the product is preferably greater than or equal to 30° C. and especially in a range of from 40 to 55° C.

Waxy Polyethylene Glycols

The waxy polyethylene glycols (A) are waxy solids at room temperature (25° C.), i.e. the solidification temperature is above 25° C., preferably in a range of 35 to 60° C., especially preferably from 45 to 60° C. They are employed in concentrations of preferably from 25 to 60% by weight, especially preferably from 30 to 50% by weight. The molecular weight preferably is in a range from 950 to 30,000 g/mol, especially preferably from 1800 to 5000, particularly from 2500 to 3500, g/mol. Polyethylene glycols have the general formula $H(OCH_2CH_2)_nOH$. The polyethylene glycols that are particularly suitable are those with n=20 to 220, preferably with n=40 to 100, especially preferably from 50 to 80. Suitable polyethylene glycols have e.g. the INCI designation PEG-20, PEG-32, PEG-40, PEG-45, PEG-55, PEG-60, PEG-75, PEG-90 or PEG-100. PEG-60 and PEG-75 are especially preferred. Commercial products usually have a molecular weight distribution. For example, polyglycol 3000 with a molecular weight of 2700 to 3000 or polyglycol 4000 of Clariant with a molecular weight of 3700 to 4500 of Clariant are suitable.

Additional Liquid Polyethylene Glycol

In a preferred embodiment an additional polyethylene glycol is included to improve the product performance, especially in regard to an improved distributability and workability into the hair. This additional polyethylene glycol is a liquid at room temperature (25° C.). The composition of the invention preferably contains the added liquid PEG (C) in an amount of from at least 15% by weight, especially preferably from 30 to 70% by weight, and more preferably from 40 to 60% by weight. The weight ratio of the solid PEG (A) to the additional liquid PEG (C) amounts to preferably from 0.5 to 1.25, especially preferably 0.6 to 1. The molecular weight of the liquid PEG (C) is preferably in a range from 100 to 700, especially preferably from 350 to 700, more preferably from 500 to 650 g/mol. Suitable liquid PEG has the formula $H(OCH_2CH_2)_nOH$ with n=4 to 14, preferably 8 to 12. Suitable liquid PEGs have the INCI names: PEG-4, PEG-6, PEG-7, PEG-8, PEG-9, PEG-10, PEG-12 and PEG-14, wherein PEG-10 and PEG-12 are especially preferred. Suitable commercial products are e.g. polyglycol 400 with a molecular weight of 380 to 420 g/mol or polyglycol 600 with a molecular weight of 570 to 630 g/mol, marketed by Clariant.

Hydrophobic Additive Substance

The hydrophobic additive substance preventing the crystallization of polyethylene glycol (A) preferably is employed in an amount of greater than 5% to greater than or equal to 30 percent by weight, especially preferably from 10 to 20 percent by weight. Suitable additive substances include hydrophobic waxes, hydrophobic soft waxy materials and hydrophobic oils.

Suitable hydrophobic waxes are, e.g., animal, vegetable, mineral and synthetic waxes, microcrystalline waxes, macrocrystalline waxes, solid paraffins, ozocerite, montan wax, Fischer-Tropsch waxes, polyolefin waxes, e.g. polybutylene, beeswax, wool wax (lanolin) and its derivative compounds, such as wool wax alcohols, candelilla wax, carnauba wax, Japan wax, hardened fats, fatty acid esters, fatty acid glycerides each with a solidification point of above 40° C., polyethylene waxes and silicone waxes. The hydrophobic waxes or wax-like materials have solidification points above 40° C., preferably above 55° C. Suitable hydrophobic soft waxy materials are for example semisolid paraffins. The solidification points of these paraffins are usually in a range of from about 25° C. to 40° C. Products with an INCI name Petrolatum, e.g. VASELINE®, are especially suitable as the hydrophobic additive substance. This latter product is a semisolid mixture of hydrocarbons obtained from petroleum.

Suitable hydrophobic oils have a melting point of under 25° C. and a boiling point preferably above 250° C., especially preferably above 300° C. For this purpose generally oils known to one skilled in the art can be used, for example vegetable or animal oils, mineral oils (Paraffinum liquidum), silicone oils or their mixtures. Suitable silicone oils are polydimethylsiloxanes, phenylated silicones, polyphenylmethylsiloxanes, phenyltrimethicones, Poly($C_1$-$C_{20}$)-alkylsiloxanes, alkylmethylsiloxanes. Hydrocarbon oils, e.g. paraffin or isoparaffin oils, squalane, oils from fatty acids and polyols, especially triglycerides, are also suitable. Suitable vegetable oils include e.g. sunflower oil, coconut oil, castor oil, lanolin oil, jojoba oil, corn oil and soybean oil.

Emulsifiers

In a preferred embodiment of the invention the hair wax product also contains at least one emulsifier. The emulsifiers are preferably contained in an amount of from 0.1 to 20 percent by weight, especially preferably from 0.2 to 10 percent by weight. The emulsifiers can be nonionic, anionic, cationic or zwitterionic. However nonionic emulsifiers are preferred. For example, the following are suitable:

ethoxylated fatty alcohol, ethoxylated fatty acid, ethoxylated fatty acid glyceride or ethoxylated alkyl phenol, especially addition products of 2 to 30 mol ethylene oxide and/or 1 to 5 mol propylene oxide to $C_8$- to $C_{22}$-fatty alcohols, to $C_{12}$- to $C_{22}$-fatty acids or to alkyl phenols with 8 to 15 carbon atoms in the alkyl groups, $C_{12}$- to $C_{22}$-fatty acid monoesters and diesters of addition products of 1 to 30 mol ethylene oxide to glycerol, addition products of 5 to 60 mol ethylene oxide to castor oil or to hardened (hydrogenated) castor oil, monoesters, diesters and/or triesters of phosphoric acid with addition products of 2 to 30 mol ethylene oxide to $C_8$- to $C_{22}$-fatty alcohols, fatty acid sugar esters, especially esters of sucrose and one or two $C_8$- to $C_{22}$-fatty acids, INCI name: Sucrose cocoate, sucrose dilaurate, sucrose distearate, sucrose laurate, sucrose myristate, sucrose oleate, sucrose palmitate, sucrose rincoleate and sucrose stearate, polyglyceryl fatty acid esters, especially of one, two or several $C_8$- to $C_{22}$-fatty acids and polyglycerides with preferably 2 to 20 glyceryl units.

In an especially preferred embodiment the emulsifiers have a waxy consistency and a dripping point above 25° C.

Pigments

In a preferred embodiment of the invention the hair wax product also includes at least one pigment. This pigment can be a colored pigment, which imparts a color effect to the product mass or the hair or it can be a luster effect pigment, which imparts a luster effect to the hair or the product mass. The color and luster effects on the hair are preferably temporary, i.e. they are maintained until the next hair washing and can be removed by washing the hair again with conventional shampoos. The pigments are present in the product mass in undissolved form. They can be contained in an amount of 0.01 to 25 percent by weight, especially preferably from 5 to 15 percent by weight.

The pigments are preferably micro-pigments, not nano-pigments. The preferred particle size amounts to from 1 to 200 μm, especially from 3 to 150 μm, especially preferably from 10 to 100 μm.

The pigments are practically insoluble coloring agents and can be inorganic or organic. Also inorganic-organic mixed pigments may be used. Inorganic pigments are preferable. The advantage of the inorganic pigments is their outstanding light-resistance, weather-resistance and temperature-resistance. The inorganic pigments can be of natural origin, for example chalk, ocher, umber, green earth, burnt siena or graphite. The pigments can be white pigments, such as titanium dioxide or zinc oxide; black pigments, such as iron oxide black; fancy or multi-colored pigments, such as ultramarine or iron oxide red; lustrous pigments, metal effect pigments, pearlescent pigments as well as fluorescene or phosphorescent pigments. Preferably at least one pigment is a colored, non-white pigment. Metal oxides, metal hydroxides and metal oxide hydrates, mixed phase pigments, sulfur-containing silicates, metal sulfides, complex metallo-cyanides, metal sulfates, metal chromates and metal molybdates and metals themselves (bronze pigments) are suitable. In particular, titanium dioxide (C.I. 77891), black iron oxide (C.I. 77499), yellow iron oxide (C.I. 77492), red and brown iron oxide (C.I. 77491), manganese violet (C.I. 77742), ultramarine (sodium aluminum sulfosilicate, C.I. 77007, Pigment Blue 29), chromium oxide hydrate (C.I.

77289), Iron Blue (Ferric ferrocyanide, C.I. 77510) and carmine (cochineal), are all suitable pigments.

Pigments based on mica and/or isinglass, which are coated with a metal oxide or metal oxychloride, such as titanium dioxide or bismuth oxychloride and if necessary other color-imparting materials, such as iron oxides, iron blue, ultramarine, carmine, etc, whose colors can be modified by changing the thickness of the coating, are especially preferred. Pigments of this sort are marketed, for example, under the trademark, Rona®, Colorona®, Dichrona® and Timiron® by the firm, Merck, Germany.

Organic pigments are, for example, the natural pigments, Sepia, gamboge, charcoal, Kasseler brown, indigo, chlorophyl and other plant pigments. Synthetic organic pigments include, for example, azo pigments, anthrquinoid pigments, indigoid pigments, dioxazine, quinacridone, phthalocyanine isoindolinone pigments, perylene pigments, perinone pigments, metal complex pigments, alkali blue pigments and diketopyrrolopyrrole pigments.

Optional Additives

In addition to the above-described ingredients the composition according to the invention can also contain the following cosmetic additive ingredients:
  solvents, such as water or a univalent or polyvalent $C_1$- to $C_4$-alcohols, such as ethanol, propanol, glycerol or glycols in an amount of up to 15 percent by weight, preferably from 0.1 to 8 percent by weight;
  dissolved cosmetic dyestuffs in an amount of up to 6 percent by weight, preferably from 0.1 to 4 percent by weight;
  perfumes and fragrances in an amount of up to 2 percent by weight, preferably from 0.01 to 1 percent by weight;
  preservatives in an amount of up to 1 percent by weight, preferably from 0.01 to 0.5 percent by weight, especially p-hydroxybenzoic acid ester, benzoic acid, salicylic acid, sorbic acid, mandelic acid, polyhexamethylene biguanidine hydrochloride or isothazolinone derivative compounds;
  film-forming polymers, such as polyvinyl pyrrolidone or vinyl pyrrolidone/vinyl acetate copolymers, in an amount of up to 5 percent by weight, preferably from 0.1 to 4 percent by weight; and
  hair care substances, such as betaine, in an amount of up to 5 percent by weight, preferably from 0.01 to 4 percent by weight.

Preferred Embodiment

A preferred embodiment of the hair wax product contains:
  (A) 30 to 60% by weight of at least one polyethylene glycol with a molecular weight in a range of 950 to 30,000 g/mol,
  (B) 10 to 30% by weight of at least one hydrophobic wax, hydrophobic soft waxy substance or hydrophobic oil,
  (C) 30 to 60% by weight of at least one polyethylene glycol with a molecular weight in a range of from 200 to 700 g/mol,
  (D) 0 to 15% by weight of at least one emulsifier,
  (E) 0 to 15% by weight water,
  (F) 0 to 10% by weight of at least one additive ingredient, selected from the group consisting of monovalent or multivalent $C_1$- to $C_5$-alcohols, perfumes, fragrances, dyes, preservatives, light-protective substances, film-forming polymers, hair care active ingredients and pearlescence imparting pigments,
wherein the needle penetration number of the product at 25° C. is greater than or equal to 10 and the solidification point is greater than or equal to 30° C.

Manufacturing Method

The hair wax products according to the invention can be made by melting and mixing the solid wax ingredients with each other. Subsequently the resulting mixture is cooled and shortly prior to solidification the volatile additive ingredients are added and mixed with it. The still flowing mass is filled in the desired container, e.g. a plastic dish, prior to solidification.

Application Method

The application of the hair wax product according to the invention is very simple. Preferably it is applied to dry hair. An amount, which can vary depending on the length of the hair, e.g. from approximately pea-size to approximately hazelnut size, is removed with the fingers. The wax is rubbed on the surface of the hand and is melted or at least softened by the heat of the hand and by shear forces during rubbing. The wax is worked into the hair in a softened or more or less liquid state and the hair is set in the desired hairstyle. Also separated or individual hair strands can be treated in order to accentuate them. The wax hardens in the hair and the hairstyle formed obtains stability, luster, texture and hold.

The hair wax product according to the invention permits individual hairstyle formation and the targeted treatment of individual hair strands because of its waxy consistency and its cohesive properties. The product mass is easily distributed on the hair. The treated hair is characterized by an outstanding luster and by a high shape stability of the hairstyle set up. The hair is not excessively loaded and the product mass is easily washed. The product mass does not partially crystallize until expiration of a longer time interval than for prior art hair wax products, so that during that time interval no graininess appears and the product appears to be homogeneous.

The following examples illustrate the subject matter of the invention in more detail without limitation of the appended claims.

EXAMPLES

Example 1

|  | A | B | C |
| --- | --- | --- | --- |
| PEG-60 | 40 g | 40 g | 40 g |
| PEG-12 | 50 g | 50 g | 25 g |
| PEG-20 | — | — | 25 g |
| Petrolatum | 10 g | — | — |
| PEG-25 Hydrogenated Castor Oil | 0.5 g | 0.5 g | 0.5 g |
| Water | — | To 100 g | To 100 g |

The contents of the composition are mixed with each other, melted at higher temperature, filled in a plastic dish and allowed to cool.

The consistency of the composition A according to the invention was compared with that of the compositions B and C, which are not of the invention. The composition A is clearly more uniform or homogeneous, less brittle or less grainy, and may be removed more easily from the container. It is distributed more easily and better with the hands and produces more luster after application to the hair than the compositions B and C, which are not of the invention.

Example 2

| 40-60 g | PEG-12 |
| 30-50 g | PEG-60 |
| 10-20 g | Petrolatum |
| q.s. | Emulsifier |
| q.s. | Perfume |

Example 3

| 40-60 g | PEG-12 |
| 30-50 g | PEG-60 |
| 0-20 g | Petrolatum |
| 5-10 g | Carnauba wax or Cera alba |
| q.s. | Emulsifier |
| q.s. | Perfume |

Example 4

| 38 g | PEG-60 |
| 50 g | PEG-12 |
| 10 g | Petrolatum |
| 0.5 g | TIMERON ® Super Silver (Mica/Titanium dioxide Pigment) |
| 0.5 g | PEG-25 Hydrogenated Castor Oil |
| 0.1 g | D-Panthenol |
| q.s. | Perfume |
| 100 g | water |

Example 5

| 38 g | PEG-60 |
| 25 g | PEG-12 |
| 25 g | PEG-20 |
| 10 g | Petrolatum |
| 0.5 g | TIMERON ® Super Silver (Mica/Titanium dioxide Pigment) |
| 0.5 g | PEG-25 Hydrogenated Castor Oil |
| 0.1 g | D-Panthenol |
| q.s. | Perfume |
| 100 g | water |

Example 6

| 33 g | PEG-60 |
| 45 g | PEG-12 |
| 20 g | Lanolin |
| 0.5 g | PEG-25 Hydrogenated Castor Oil |
| q.s. | Perfume |

The disclosures in German Patent Applications DE 102 52 167.0 and EP 030 01 081.3 of Nov. 9, 2002 and Jan. 18, 2003 respectively are incorporated here by reference. These German Patent Applications describes the invention described hereinabove and claimed in the claims appended hereinbelow and provide the basis for a claim of priority under 35 U.S.C. 119.

While the invention has been illustrated and described as embodied in a hair wax product containing polyethylene glycol waxes and hydrophobic substances, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair wax product consisting of:
   from 30 to 60% by weight of at least one waxy polyethylene glycol with a molecular weight in a range of from 950 to 30,000 g/mol,
   from 10 to 30% by weight of at least one additive substance that prevents crystallization of said at least one waxy polyethylene glycol, wherein said at least one additive substance is selected from the group consisting of semisolid paraffins with a solidification point in a range from about 25° C. to 40° C.,
   from 30 to 60% by weight of at least one additional polyethylene glycol with a molecular weight in a range of from 200 to 700 g/mol and which is a liquid at 25° C.,
   from 0.2 to 15% by weight of at least one nonionic emulsifier,
   from 0 to 15% by weight water,
   from 0 to 10% by weight of at least one cosmetic auxiliary selected from the group consisting of monovalent $C_1$- to $C_5$-alcohols, multivalent $C_1$- to $C_5$-alcohols, perfumes, fragrances, dyes, preservatives, film-forming polymers, hair care active ingredients and inorganic pigments;
   and having a needle penetration number greater than or equal to 10 at 25° C. and a solidification point greater than or equal to 30° C.

2. The hair wax product as defined in claim 1, wherein a weight ratio of said at least one waxy polyethylene glycol to said at least one additional polyethylene glycol is from 0.5 to 1.25.

3. The hair wax product as defined in claim 1, wherein said at least one additive substance is petrolatum and said at least one nonionic emulsifier is an addition product of 5 to 60 mol ethylene oxide to castor oil or hydrogenated castor oil.

4. The hair wax product as defined in claim 1, wherein said at least one nonionic emulsifier is selected from the group consisting of ethoxylated fatty alcohols, ethoxylated fatty acids, ethoxylated fatty acid glycerides, ethoxylated alkyl phenols, $C_{12}$- to $C_{22}$-fatty acid monoesters of addition products of 1 to 30 mol ethylene oxide to glycerol, $C_{12}$- to $C_{22}$-fatty acid diesters of addition products of 1 to 30 mol ethylene oxide to glycerol, addition products of 5 to 60 mol ethylene oxide to castor oil, addition products of 5 to 60 mol ethylene oxide to hardened (hydrogenated) castor oil, monoesters of phosphoric acid with addition products of 2 to 30 mol ethylene oxide to $C_8$- to $C_{22}$-fatty alcohols, diesters of phosphoric acid with addition products of 2 to 30 mol ethylene oxide to $C_8$- to $C_{22}$-fatty alcohols, triesters of phosphoric acid with addition products of 2 to 30 mol ethylene oxide to $C_8$- to $C_{22}$-fatty alcohols, fatty acid sugar esters and polyglyceryl fatty acid esters.

* * * * *